United States Patent [19]

Sawano

[11] Patent Number: 5,653,113
[45] Date of Patent: Aug. 5, 1997

[54] COOLING SYSTEM

[75] Inventor: Masahito Sawano, Tokyo, Japan

[73] Assignee: Rigaku Corporation, Tokyo, Japan

[21] Appl. No.: 627,285

[22] Filed: Apr. 4, 1996

[30] Foreign Application Priority Data

Apr. 7, 1995 [JP] Japan ................... 7-082296
May 15, 1995 [JP] Japan ................... 7-115833

[51] Int. Cl.$^6$ ............................................. F25B 19/00
[52] U.S. Cl. ................................ 62/51.1; 62/55.5
[58] Field of Search ........................... 62/51.1, 55.5

[56] References Cited

U.S. PATENT DOCUMENTS

| | | | |
|---|---|---|---|
| 3,769,806 | 11/1973 | Boissin et al. | 62/55.5 |
| 4,295,339 | 10/1981 | Kuraoka et al. | 62/51.1 |
| 4,495,782 | 1/1985 | Salour et al. | 62/51.1 |
| 4,559,787 | 12/1985 | Batzer et al. | 62/55.5 |
| 4,848,093 | 7/1989 | Simmonds et al. | 62/51.1 |
| 5,193,348 | 3/1993 | Schnapper | 62/51.1 |
| 5,299,425 | 4/1994 | Hingst | 62/51.1 |

*Primary Examiner*—Ronald C. Capossela
*Attorney, Agent, or Firm*—Armstrong, Westerman, Hattori, McLeland & Naughton

[57] ABSTRACT

There is provided a cooling chamber which communicates with a nozzle pipe. A heat absorption portion is formed on an outer peripheral surface of an expansion chamber of a cryopump and the heat absorption portion is disposed inside the cooling chamber. For example, ordinary temperature nitrogen gas is supplied to the cooling chamber as a cooling medium, the heat of the nitrogen gas is absorbed by the heat absorption portion of the cryopump, and then the nitrogen gas is jetted from a tip end opening of the inner pipe. With such an arrangement, it is possible to easily cool an object to be cooled such as a sample using a cooling medium which costs less than liquid nitrogen. Further, the nozzle pipe has a triple-structured arrangement comprising an inner pipe, a vacuum adiabatic pipe and an outer pipe, wherein the vacuum adiabatic pipe has a tapered surface at a tip end periphery thereof in which a diameter of the vacuum adiabatic pipe is gradually reduced toward the tip end of the inner pipe, thereby preventing the current of the drying medium from being turbulent at the tip opening of the inner pipe 11 and also preventing fresh air including humidity from turning around and directing toward the inner pipe 11. As a result, frost is prevented from adhering to the tip end of the inner pipe, thereby facilitating stabilization of cooling performance.

3 Claims, 3 Drawing Sheets

COOLING SYSTEM

BACKGROUND OF THE INVENTION

1. Field of the Invention

The present invention relates to a cooling system suitably adapted for cooling a sample mounted on a measuring apparatus such as an X-ray diffractometer.

2. Prior Art

In measuring a sample using a measuring apparatus such as an X-ray diffractometer, the sample serving as a measuring object is first rendered cryogenic, and then it is diffracted in its crystal structure, etc. in such a state. In such a measurement, a cooling system is employed for rendering the sample cryogenic.

As a prior cooling system of this type, there is known an arrangement in which liquid nitrogen is first stored in a storage tank, then it is rendered gaseous by a suitable amount, and thereafter it is supplied to a nozzle pipe so that low-temperature nitrogen gas is jetted toward the sample through the tip end of the nozzle pipe.

FIG. 4 is a view showing an arrangement of the prior art cooling system of this type. As shown in the same figure, liquid nitrogen is first sealed and stored in a storage tank 100, and then it is heated by a heater 101 so that it is rendered gaseous by a suitable amount and is changed to nitrogen gas. The nitrogen gas thus generated is supplied to a nozzle body 103 through a pipe 102 coupled to the nozzle body 103. In the nozzle body 103, the temperature of the nitrogen gas is changed to a proper value by a temperature control heater 105 while it is controlled by a thermo couple 104, then the nitrogen gas is jetted from a tip end opening of a nozzle pipe 106 coupled to the nozzle body 103.

The liquid nitrogen is changed to dry gas when moisture thereof is removed by a drying heater 107 coupled to the storage tank 100, and the thus changed dry gas is supplied to an outer periphery of the nozzle pipe 106 through a pipe 108 coupled to the drying heater 107. As a result, it is possible to prevent frost from adhering to the tip end of the nozzle pipe 106 when the dry gas is supplied or jetted from the pipe 108 to the tip end of the nozzle pipe 106.

As mentioned above, the prior art cooling system of this type uses liquid nitrogen as a cooling medium. The liquid nitrogen is generally expensive. Further, careful attention must be paid when the liquid nitrogen is carried or handled, and it is sometimes difficult to be carried depending on the location where it is used, whereby the measurement of the sample is sometimes difficult to perform.

For example, it is not unusual that a X-ray diffraction measurement lasts for a long period of time of more than one week. There occurs such problems in that first the amount of liquid nitrogen used during the period sometimes exceeds, e.g. 100 liter, secondly it takes time and labor to carry and supply the liquid nitrogen, and thirdly it is expensive.

On the other hand, there are following problems for the structure of the nozzle pipe 106.

FIG. 5 is an enlarged cross sectional front view showing the tip end of the nozzle pipe used for a prior art cooling system.

As shown in FIG. 5, the nozzle pipe 106 of this type is a triple-structured pipe comprising an inner pipe 201, an outer pipe 202 and a vacuum adiabatic pipe 203, which is coaxially arranged between the inner pipe 201 and the outer pipe 202.

That is, the vacuum adiabatic pipe 203 is provided coaxially around the outer periphery of the inner pipe 201 with a given interval, and the outer pipe 202 is also provided coaxially around the outer periphery of the vacuum adiabatic pipe 203 with a given interval. The tip end 203a of the vacuum adiabatic pipe 203 is closed at a position a little behind the tip end of the inner pipe 201. An adiabatic space 204 is formed between the vacuum adiabatic pipe 203 and the inner pipe 201. Air in the adiabatic space 204 is attracted by a vacuum pump, not shown, to thereby render the inner pipe 201 adiabatic.

Nitrogen gas serving as a cooling medium is passed through the inner pipe 201 and is jetted from the tip end opening thereof. There is a method of blowing dry gas toward the tip end of the nozzle pipe 106 through a tip end of a pipe 108 which is provided separately from the nozzle pipe 106 (refer to FIG. 4) to prevent frost from adhering to the tip end of the nozzle pipe 106. However, there are the following drawbacks in this method. That is, an operation to install or connect the nozzle pipe 106 and the pipe 108 to a measuring apparatus is troublesome, and a jetting direction of the nitrogen gas is liable to be changed when the dry gas is blown out from different directions.

Accordingly, the nozzle pipe 106 has a structure as shown in FIG. 5 in which dry gas is supplied to a space defined between the outer pipe 202 and the vacuum adiabatic pipe 203 and it is jetted from the tip end opening of the outer pipe 202, thereby preventing frost from adhering to the tip end of the inner pipe 201.

Use of this nozzle in the arrangement of FIG. 4 can dispense with the pipe 108, thereby facilitating the installation of the nozzle pipe 106 and preventing the jetting direction of the nitrogen gas from being changed by the dry gas.

However, when analyzing the structure of the tip end of the nozzle pipe 106, the tip end (closed end) 203a of the vacuum adiabatic pipe 203 has a stepped shape, and a tip end portion 201a of the inner pipe 201 is slightly extended from the vacuum adiabatic pipe 203.

Accordingly, there occurs frequently such a problem that the turbulence of dry air current is generated in a space extending from the tip end 203a (stepped shape) of the vacuum adiabatic pipe 203 to the tip end opening of the outer pipe 202 so that fresh air including humidity turns around and directs toward the tip end of the inner pipe 201.

When the fresh air including humidity adheres to the tip end of the inner pipe 201, even if the amount of moisture adhered thereto is very slight, there is a possibility that the humidity or moisture adhered to the tip end of the inner pipe 201 is changed to frost and the frost grows to thereby lower cooling performance, especially when a measurement takes a long period of time (there is a possibility of a continuous measurement lasting for more than one week for analyzing a single-crystal sample using an X-ray diffractometer).

SUMMARY OF THE INVENTION

The present invention has been made to solve the problems of the prior art cooling system and it has an object to easily and effectively cool an object to be cooled such as a sample using a cooling medium which is lower in cost than liquid nitrogen.

It is another object of the present invention to prevent moisture from adhering to a tip end of a nozzle pipe, thereby facilitating stabilization of cooling performance.

To achieve the above objects, the cooling system of the present invention includes the following constitutional elements:

(1) a nozzle pipe for jetting cooling medium from a tip end opening thereof;

(2) a cooling chamber which communicates with a base end opening of the nozzle pipe and has an opening for receiving the cooling medium; and (3) a cooling means including a compression chamber and an expansion chamber which communicate with each other by way of refrigerant flow paths through which cooling gas circulates, a cryopump having a heat absorption portion formed on an outer upper surface of the expansion chamber, and the like. The heat absorption portion of the cooling means is disposed inside the cooling chamber.

The cooling system having the aforementioned arrangement can use, e.g. ordinary temperature nitrogen gas, etc. as the cooling medium, and supplies this nitrogen gas to the cooling chamber. The heat absorption portion of the cooling means disposed inside the cooling chamber absorbs ambient heat when the cooling means performs heat exchange.

Accordingly, the temperature of cooling medium supplied to the cooling chamber is absorbed by the cooling means so that it is lowered. When the cooling medium, which is cooled in such a manner, is jetted toward the sample, etc. through the nozzle pipe, the sample can be cooled.

There is no inconvenience even if the cooling medium to be supplied to the cooling chamber has ordinary temperature since the temperature of the cooling medium is lowered in the cooling chamber, resulting in dispensing with the use of the liquid nitrogen, which is expensive and is inconvenient for handling.

The nozzle pipe of the present invention among the constitutional elements as mentioned above can be structured as follows to stabilize the cooling performance.

That is, the nozzle pipe is formed of a triple-structured arrangement comprising an inner pipe having a tip end opening, a vacuum adiabatic pipe, and an outer pipe in which the cooling medium is jetted through a tip end opening of the inner pipe.

The vacuum adiabatic pipe is provided coaxially around the outer periphery of the inner pipe with a given interval. The tip end of the vacuum adiabatic pipe is closed at a position which is substantially flush with the tip end of the inner pipe. Further, the vacuum adiabatic pipe has a tapered surface at a tip end periphery thereof in which a diameter of the vacuum adiabatic pipe is gradually reduced toward the tip end of the inner pipe.

The outer pipe is provided coaxially around the outer periphery of the vacuum adiabatic pipe with a given interval. The tip end of the outer pipe is positioned at a position close to the tip end of the inner pipe. The drying medium is jetted from a tip end opening of the outer pipe.

The cooling medium such as low-temperature nitrogen gas is supplied to the inner pipe. A space defined between the inner pipe and the vacuum adiabatic pipe forms a vacuum adiabatic layer when the space is rendered low-pressure, thereby rendering the outer periphery of the inner pipe adiabatic. The drying medium, such as dry air, is supplied to a space defined between the outer pipe and the vacuum adiabatic pipe, and it is jetted from the tip end opening of the outer pipe.

The drying medium jetted from the tip end opening of the outer pipe flows along the tapered surface formed at the tip end periphery of the vacuum adiabatic pipe and reaches the tip end of the nozzle pipe without staying in the space between the vacuum adiabatic pipe and the outer pipe. Both mediums jetted out of the pipe flow together in a smooth laminar flow.

Since the drying medium flows without generating turbulence of dry air current at the tip end periphery of the vacuum adiabatic pipe, there is no likelihood that the fresh air including humidity turns around and directs toward the inner pipe. As a result, there is no likelihood that frost adheres to the tip end opening of the inner pipe, thereby preventing deterioration of cooling performance.

DETAILED DESCRIPTION OF THE PREFERRED EMBODIMENT

Figure 1:
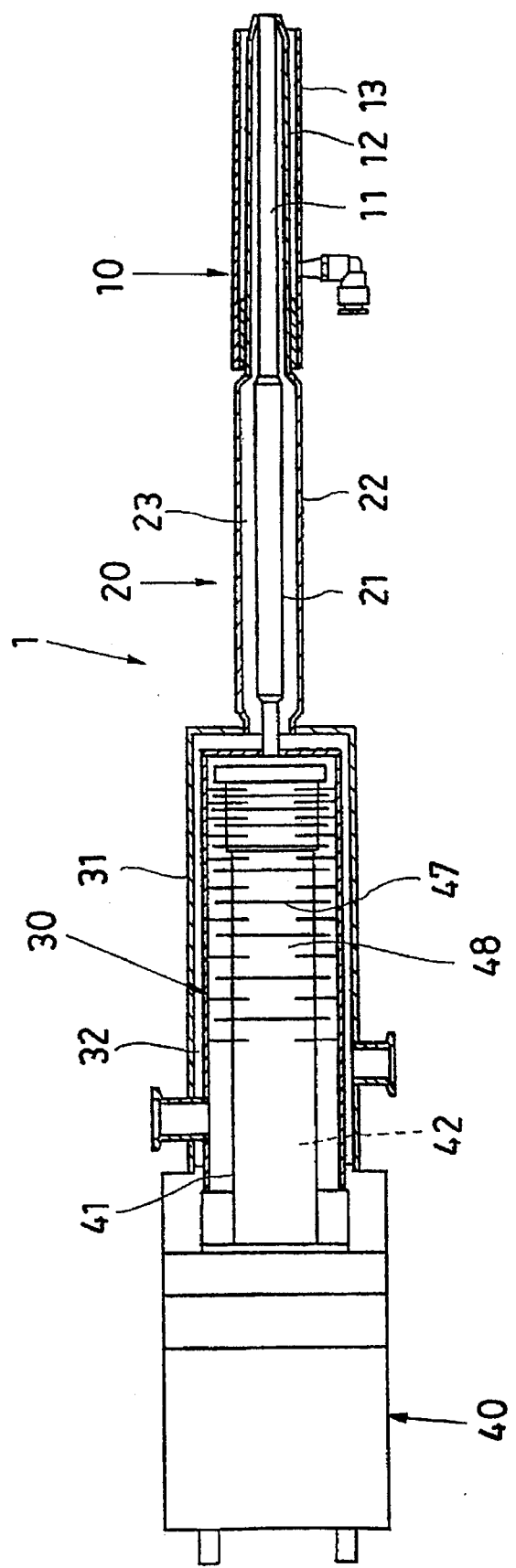
FIG. 1 is a cross sectional front view showing a main body of a cooling system according to a preferred embodiment of the present invention.

A preferred embodiment of the present invention will be now described in detail with reference to the attached drawings.

A cooling system is set up as an annex to a sample measuring device such as an X-ray diffractometer for jetting a cryogenic cooling medium toward a sample, and it comprises a main body 1, a nozzle pipe 10, a flexible pipe 20, a cooling chamber 30, and a cryopump 40 as a cooling means.

Figure 3:
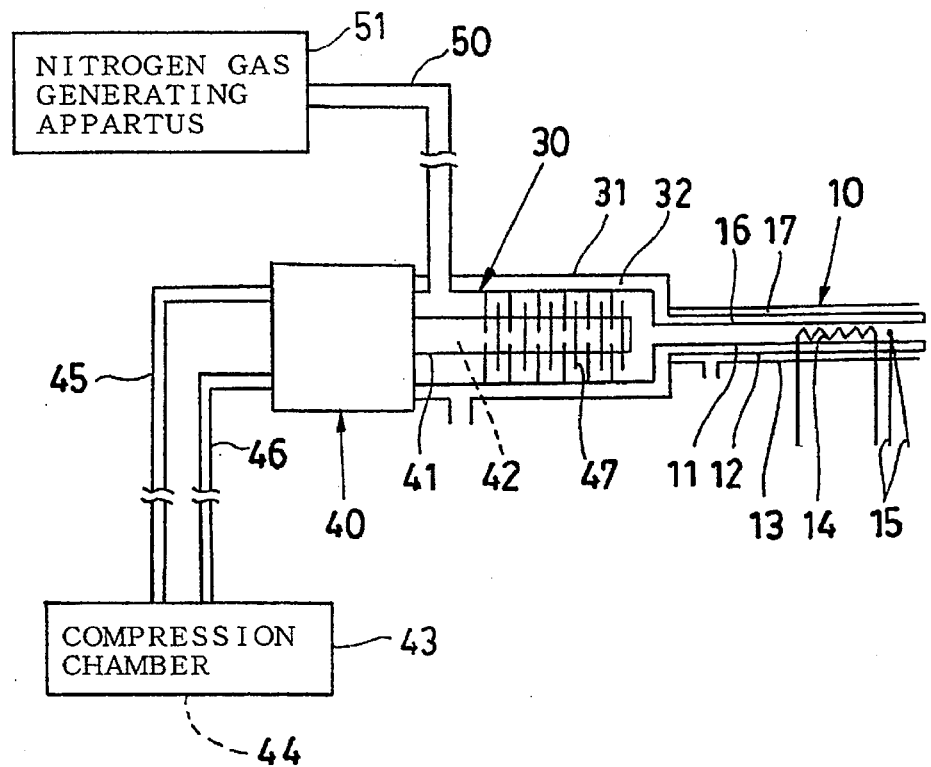
FIG. 3 is a view showing an entire arrangement of the cooling system according to a preferred embodiment of the present invention.
Figure 4:
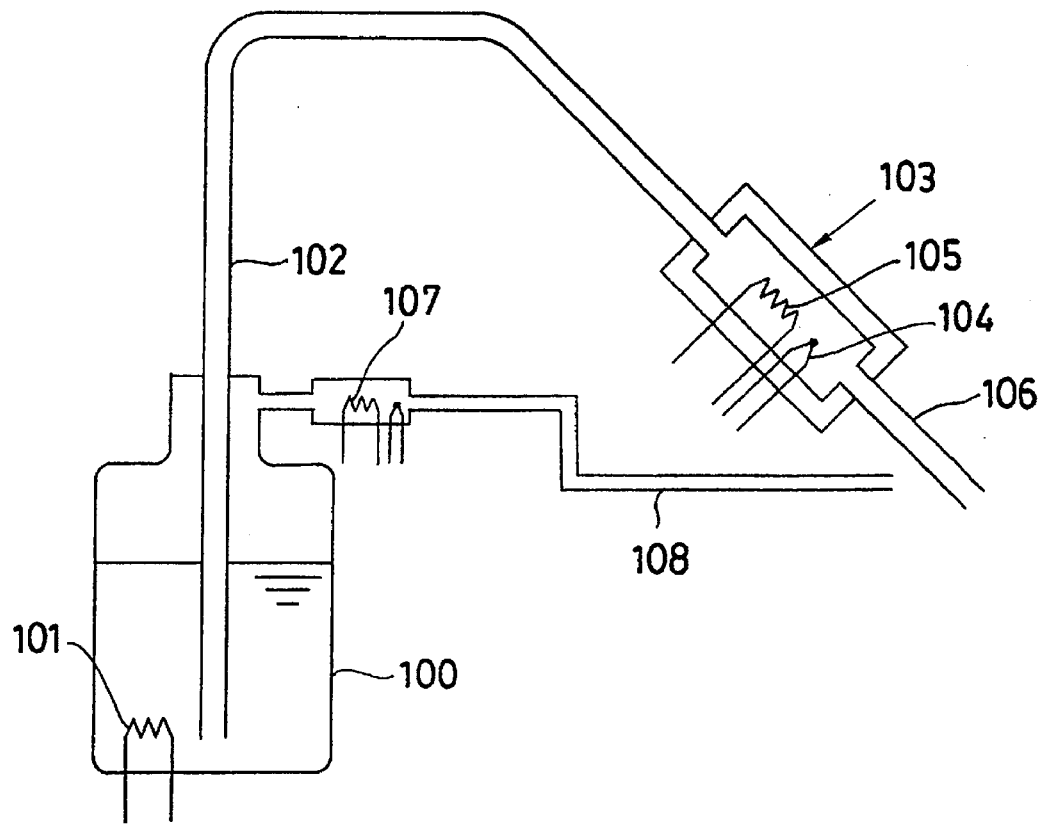
FIG. 4 is a view showing an entire arrangement of the prior art cooling system.
Figure 5:
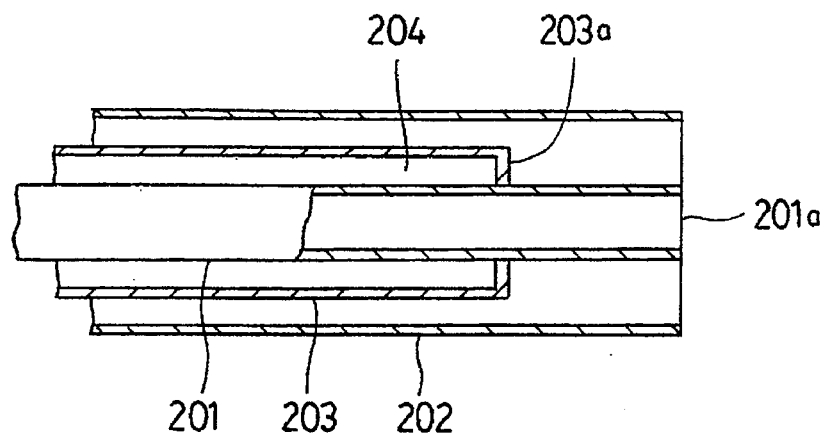
FIG. 5 is an enlarged cross sectional front view showing a tip end of a nozzle pipe used for the prior art cooling system.

FIG. 3 omits the flexible pipe 20.

Figure 2:
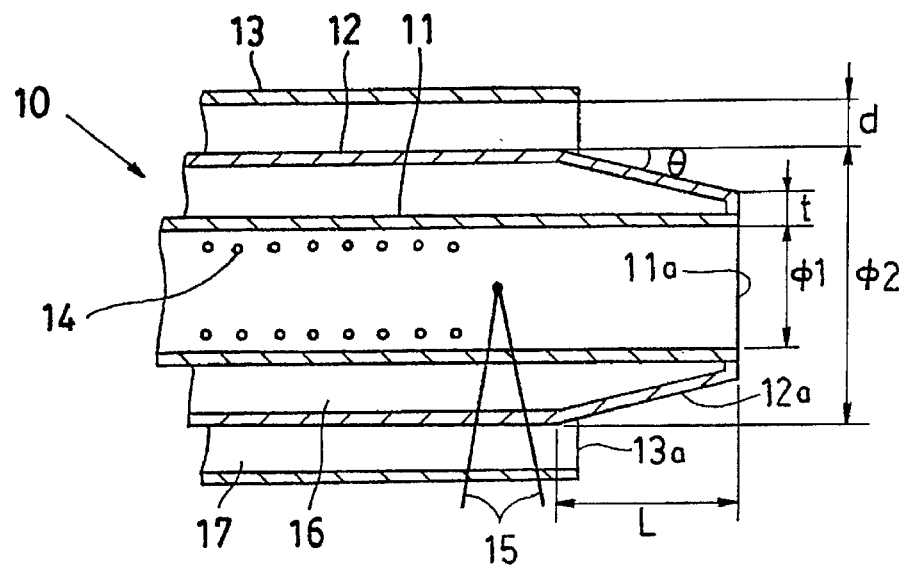
FIG. 2 is an enlarged cross sectional front view showing a tip end of a nozzle pipe of the main body in FIG. 1.

As shown in FIG. 2, the nozzle pipe 10 has a triple-structured arrangement which comprises the nozzle pipe 10, an inner pipe 11, a vacuum adiabatic pipe 12, and an outer pipe 13.

The inner pipe 11 jets cooling medium, which is supplied from the cooling chamber 30 through the flexible pipe 20, through a tip end opening 11a thereof. There are provided a temperature control heater 14 and a thermo couple 15 inside the inner pipe 11, whereby the temperature of the cooling medium is adjusted to reach a desired value of temperature when heated by the temperature control heater 14, while it is controlled by the thermo couple 15 in temperature.

The vacuum adiabatic pipe 12 is provided coaxially around the outer periphery of the inner pipe 11 with a given interval. Air in a space defined between the inner pipe 11 and the vacuum adiabatic pipe 12 is attracted by a vacuum pump and is rendered low-pressure, thereby forming an adiabatic space 16. A tip end of the vacuum adiabatic pipe 12 is closed at a position which is substantially flush with the tip end of the inner pipe. The outer pipe 13 is provided coaxially around the outer periphery of the vacuum adiabatic pipe 12 with a given interval.

A supply source, not shown, of a drying medium (such as dry air) is connected to a base end of the outer pipe 13 by way of a pipe so as to supply the drying medium in a space 17 defined between the outer pipe 13 and the vacuum adiabatic pipe 12. The thus supplied drying medium flows along an outer peripheral surface of the vacuum adiabatic pipe 12 in an axial direction thereof, and it is jetted through a tip end opening 13a of the outer pipe 13.

Further, the vacuum adiabatic pipe 12 has a tapered surface 12a at a tip end periphery thereof in which the diameter of the vacuum adiabatic pipe 12 is gradually reduced toward the tip end of the inner pipe 11 (refer to FIG. 2). The tapered surface 12a is formed to jet the drying medium through the tip end opening 13a of the outer pipe 13 without generating turbulence of dry air current, thereby preventing fresh air including humidity from adhering to the tip end opening 11a of the inner pipe 11 and the tapered surface 12a of the vacuum adiabatic pipe 12, thereby also preventing the fresh air from being frozen.

The inventor performed the following test regarding the tapered surface 12a.

The drying medium having a flow rate of 5–7 l/min is jetted from the tip end opening 13a of the outer pipe 13 under the condition that an inner diameter $\phi 1$ of the inner pipe 11 is $\phi 1=8$ mm, an outer diameter $\phi 2$ of the vacuum adiabatic pipe 12 is $\phi 2=14$ mm, a thickness t of the vacuum adiabatic pipe 12 at the tip end is t=1.0–1.5 mm, and an interval d between the vacuum adiabatic pipe 12 and the outer pipe 13 is d=1.5–2.5 mm.

When an inclination $\theta$ relative to a central axis and a length L in the axial direction are varied under the same condition, the tapered surface 12a of the vacuum adiabatic pipe 12 having an inclination expressed by $\theta=14°–16°$ and a length expressed by L=8–10 mm generates a streamlined smooth flow of drying medium, thereby preventing the current of the drying medium from being turbulent at the tip opening of the inner pipe 11 and also preventing the fresh air including humidity from turning around and directing toward the inner pipe 11.

It is preferable to appropriately adjust the inclination and the length of the tapered surface 12a formed on the tip end periphery of the vacuum adiabatic pipe 12 depending on the determined dimensions and the shape of the periphery.

Meanwhile, the test performed by the inventor showed that the fresh air is effectively prevented from turning around and directing toward the inner pipe 11 when the distance d between the outer peripheral surface of the vacuum adiabatic pipe 12 and the inner peripheral surface of the outer pipe 13 is set to be 1.5–2.5 mm, and the inclination of the tapered surface 12a relative to the central axis of the vacuum adiabatic pipe 12 is set to be 14°–16° regardless of the inner diameter of the inner pipe 11.

Each of the dimensions of the nozzle pipe 10 is not limited to those as set forth above when carrying out the invention, and hence, needless to say, the nozzle pipe 10 can be varied in its design, if need be.

The flexible pipe 20 comprises an inner pipe 21 and a vacuum adiabatic pipe 22 in which the vacuum adiabatic pipe 22 is provided coaxially with the inner pipe 21 and spaced from an outer peripheral surface of inner pipe 21 by a given interval, thereby forming a double-structured arrangement.

The inner pipe 21 and the vacuum adiabatic pipe 22 constituting the flexible pipe 20 have a bellows type structure so as to be bent elastically, although this is omitted in FIG. 1. Meanwhile, the inner pipe 21 is connected to the inner pipe 11 of the nozzle pipe 10 at the tip end thereof. The vacuum adiabatic pipe 22 is connected to the vacuum adiabatic pipe 12 of the nozzle pipe 10 at the tip end thereof. A space (adiabatic space) 23 defined between the inner pipe 21 and the vacuum adiabatic pipe 22 communicates with the adiabatic space 16 of the nozzle pipe 10.

The cooling chamber 30 is covered with a vacuum adiabatic cover 31 at its peripheral surface, and an adiabatic space 32 is defined between the cooling chamber 30 and the vacuum adiabatic cover 31. The adiabatic space 32 communicates with the adiabatic space 23 inside the flexible pipe 20. Air in each of the adiabatic spaces 32, 23 and 16 is attracted by a vacuum pump (not shown) through a pipe, and hence it is substantially rendered in a vacuum state. Exterior heat is prevented from entering the inside of the nozzle pipe 10 by way of these spaces which are rendered in a vacuum state.

The cooling chamber 30 communicates with the inner pipe 21 of the flexible pipe 20 at the tip end central portion thereof. Further, a supply source of the cooling medium is connected to the cooling chamber 30 by way of a pipe 50 (refer to FIG. 3).

According to this embodiment, ordinary temperature nitrogen gas is used as the cooling medium, and a nitrogen gas generating apparatus 51 is used as the supply source of the cooling medium. The nitrogen gas generating apparatus 51 separates nitrogen from air and takes it out from the air, and various arrangements of nitrogen gas generating apparatuses are well known.

For example, the nitrogen gas generating apparatus 51 of the PSA (Pressure Swing Adsorption) type has a structure equipped with an adsorption cylinder which is filled with adsorbent made of carbon. When air is supplied to the adsorption cylinder and is repeatedly increased and reduced in pressure, the adsorbent adsorbs gasses included in the air except nitrogen gas when it is pressurized, and emits the adsorbed gasses outside the nitrogen gas generating apparatus when it is reduced in pressure. In such a manner, the nitrogen gas generating apparatus of this type can separate nitrogen from air.

When the nitrogen gas generating apparatus 51 is used as the supply source of the cooling medium, it is not necessary to carry the liquid nitrogen as in the prior art, leading to a remarkable simplification of the preparing operation for the measurement.

A cryopump main body 41 is attached to the base end of the cooling chamber 30. The cryopump 40 has a structure for circulating a cooling gas (helium), and for repeatedly compressing and expanding the cooling gas, thereby performing heat exchange. The cryopump 40 is known as a small vacuum pump equipped with an adsorption plate which adsorbs and catches ambient gasses due to a heat absorbing operation involved in the expansion of the cooling gas.

According to the preferred embodiment, the cooling medium supplied to the cooling chamber 30 is cooled utilizing the cryopump 40, and it is jetted through the tip end of the nozzle pipe 10.

The arrangement of the cryopump 40 is further described with reference to FIG. 3. The expansion chamber 42 is formed inside the cryopump main body 41. A compression chamber 44 is formed inside a compressor 43 which is provided separately from the cryopump main body 41. The compression chamber 44 and the expansion chamber 42 communicate with each other by a supply pipe 45 and a discharge pipe 46 so as to circulate the cooling gas.

An adsorption plate is normally attached to an outer peripheral surface of the cryopump main body 41 for adsorbing ambient gasses utilizing adsorbent such as active carbon. However, according to the preferred embodiment, the adsorption plate is removed, and cooling fins 47 for absorbing heat are arranged are formed on the outer peripheral surface of the cryopump main body 41 with given intervals, thereby forming a heat absorption portion 48.

The heat absorption portion 48 is disposed inside the cooling chamber 30, and there is formed a flow path through which the cooling medium introduced from the base end side of the cooling chamber 30 is supplied to the inner pipe 21 of the flexible pipe 20 through the heat absorption portion 48.

Since the cooling chamber 30 communicates with the flexible pipe 20, the cooling medium, heat of which is absorbed inside the cooling chamber 30, flows to the nozzle pipe 10 through the flexible pipe 20 in a cryogenic state, then it is jetted through the tip end of the nozzle pipe 10.

The operation of the cooling system of the present invention will be now described.

The cooling chamber 30 to which the cryopump main body 41 is attached, the flexible pipe 20 and the nozzle pipe 10 are integrated with one another to form the main body 1. The main body 1 is installed on a measuring apparatus such as an X-ray diffractometer. At this time, the tip end of the nozzle pipe 10 is disposed close to and is directed to a sample.

Then, the compressor 43 is operated so as to start heat exchange in the cooling gas, and the nitrogen gas generating apparatus 51 is operated so as to take nitrogen gas from the atmosphere and supply it as a cooling medium to the cooling chamber 30.

The cryopump 40 compresses the cooling gas in the compression chamber 44 inside the compressor 43 and emits the heat of the cooling gas. Thereafter, the cryopump 40 supplies the cooling gas under pressure to the expansion chamber 42 inside the cryopump main body 41 by way of the supply pipe 45.

The cooling gas enters the expansion chamber 42 and is sharply increased in volume and is decreased in temperature so that it performs heat exchange with an outside gas by way of the heat absorption portion 48.

Since the heat absorption portion 48 is disposed inside the cooling chamber 30, the heat of the nitrogen gas (cooling medium), which is supplied to the cooling chamber 30 for the heat exchange, is absorbed and is changed to low-temperature nitrogen gas.

The cooling gas, which absorbed heat from the nitrogen gas inside the cooling chamber 30, is supplied to the compression chamber 44 inside the compressor 43 through the discharge pipe 46, and it is again subjected to a compression and radiation operation.

The nitrogen gas, heat of which is absorbed in the cooling chamber 30, is supplied from the inner pipe 21 to the inner pipe 11, then the temperature of the nitrogen gas is controlled to a desired value by the temperature control heater 14 inside the inner pipe 11, and finally it is jetted to the sample through the tip end opening 11a of the inner pipe 11.

Air in the adiabatic spaces 32, 23 and 16 respectively formed in the cooling chamber 30, the flexible pipe 20, and inside the nozzle pipe 10 is attracted by a vacuum pump, not shown, so that the cooling chamber 30, and each of the inner pipes 21 and 11 is rendered adiabatic.

Dry air is introduced from a supply source of a drying medium, not shown, to the space 17 defined between the vacuum adiabatic pipe 12 and the outer pipe 13, and it is jetted through the tip end opening 13a of the outer pipe 13.

Accordingly, a dry air layer is formed around cryogenic nitrogen gas, which is jetted from the inner pipe 11, so as to effectively jet the nitrogen gas to the sample while preventing the nitrogen gas from being scattered.

Whereupon, since dry air flows smoothly along the tapered surface 12a formed at the tip end periphery of the vacuum adiabatic pipe 12, wet fresh air does not turn around and direct into the nozzle pipe 10, thereby preventing the fresh air from being frozen.

The present invention is not limited to the aforementioned embodiment.

For example, the flexible pipe 20 may be omitted and the nozzle pipe 10 and the cooling chamber 30 may be directly connected with each other as shown in FIG. 3.

Further, the supply source of the cooling medium is not limited to the nitrogen gas generating apparatus. The nitrogen gas generating apparatus may be replaced by a gas cylinder into which a cooling medium such as nitrogen gas, or hydrogen gas is sealed. It is convenient to use the nitrogen gas generating apparatus capable of dispensing with carriage and replenishment of the cooling medium in an area where cooling medium such as nitrogen gas and hydrogen gas is difficult to be made available.

The cooling means is not limited to the cryopump, but the cryopump may be replaced by a variety of small heat exchangers having a heat absorption portion which can be disposed inside the cooling chamber.

Further, the cooling system of this invention can be applied to various objects where it is needed to render a relatively small spot or area cryogenic, for example, it can be used in a cooling system for medical treatment for cooling an affected part of the human body.

The effect of the present invention will be now described.

The cooling system of the present invention has the heat absorption portion of the cooling means such as the cryopump which is disposed inside the cooling chamber communicating with the nozzle pipe, wherein cooling medium supplied to the cooling chamber is cooled due to a heat absorbing operation by the heat absorption portion. Accordingly, the cooling medium to be supplied to the cooling chamber is not needed to be a cryogenic medium such as liquid nitrogen so that a sample to be cooled can be easily and effectively cooled by a cooling medium such as nitrogen gas which costs less than liquid nitrogen. Accordingly, it is possible to reduce the cost of the cooling medium.

Further, the nozzle pipe has a triple-structured arrangement comprising the inner pipe, the vacuum adiabatic pipe and the outer pipe wherein the vacuum adiabatic pipe has the tapered surface at the tip end periphery thereof in which a diameter of the vacuum adiabatic pipe is gradually reduced toward the tip end of the inner pipe, thereby preventing the current of the drying medium from being turbulent at the tip opening of the inner pipe 11 and also preventing the fresh air including humidity from turning around and directing toward the inner pipe 11. As a result, frost is prevented from adhering to the tip end of the inner pipe, thereby facilitating stabilization of cooling performance.

We claim:

1. A cooling system comprising a nozzle pipe for jetting cooling medium from a tip end opening thereof, a cooling chamber communicating with a base end opening of said nozzle pipe and having a supply port through which the cooling medium is supplied, a cooling means having a compression chamber and an expansion chamber communicating with each other by way of refrigerant flow paths through which cooling gas circulates, and a heat absorption portion formed on an outer peripheral surface of said expansion chamber, wherein said heat absorption portion is disposed inside said cooling chamber.

2. A cooling system according to claim 1, wherein said cooling means is a cryopump.

3. A cooling system according to claim 1, wherein said nozzle pipe comprises an inner pipe having a tip end opening through which cooling medium is jetted, a vacuum adiabatic pipe provided coaxially around an outer periphery of the inner pipe with a given interval; said vacuum adiabatic pipe having a tip end, said tip end being closed and substantially flush with the tip end of the inner pipe, and an outer pipe provided coaxially around an outer periphery of the vacuum adiabatic pipe with a given interval; said outer pipe having a tip end positioned at a position close to the tip end opening of the inner pipe for projecting drying medium; wherein the vacuum adiabatic pipe has a tapered surface at a tip end periphery thereof in which a diameter of the vacuum adiabatic pipe is gradually reduced toward the tip end of the inner pipe.

* * * * *